United States Patent [19]

Lai et al.

[11] Patent Number: 4,899,053

[45] Date of Patent: Feb. 6, 1990

[54] SOLID STATE NON-DISPERSIVE IR ANALYZER USING ELECTRICAL CURRENT-MODULATED MICROSOURCES

[75] Inventors: N. C. Joseph Lai, Brookfield; Edward J. Zuperku, Elm Grove; Roy A. Henning, Milwaukee, all of Wis.

[73] Assignee: Criticare Systems, Inc., Waukesha, Wis.

[21] Appl. No.: 111,621

[22] Filed: Oct. 21, 1987

[51] Int. Cl.[4] ........................ G01N 21/31; G01N 21/35
[52] U.S. Cl. .................................. 250/343; 250/573; 356/437
[58] Field of Search ...................... 250/343, 345, 573; 356/437

[56] References Cited

U.S. PATENT DOCUMENTS

| | | | |
|---|---|---|---|
| 2,692,950 | 10/1954 | Wallace | 250/351 |
| 3,043,956 | 7/1962 | Cohen | 250/350 |
| 3,379,883 | 4/1968 | Ward et al. | 250/351 |
| 3,825,756 | 7/1974 | Weiss | 250/343 |
| 3,875,413 | 4/1975 | Bridgham | 250/492 |
| 3,898,462 | 8/1975 | Ishida et al. | 250/344 |
| 3,898,770 | 7/1975 | Takami et al. | 356/96 |
| 4,013,260 | 3/1977 | McClatchie et al. | 250/343 |
| 4,044,257 | 8/1977 | Kreuzer | 250/344 |
| 4,200,791 | 4/1980 | Burough | 250/343 |
| 4,205,913 | 6/1980 | Ehrfeld et al. | 356/72 |
| 4,260,883 | 4/1981 | Onoda et al. | 250/345 |
| 4,303,343 | 12/1981 | Patel et al. | 356/432 |
| 4,322,621 | 3/1982 | Aagard | 250/343 |
| 4,423,739 | 1/1984 | Passaro et al. | 128/179 |
| 4,437,005 | 3/1984 | Ophoff et al. | 250/343 |
| 4,467,203 | 8/1984 | Rappaport | 250/345 |
| 4,489,239 | 12/1984 | Grant et al. | 250/339 |
| 4,500,207 | 2/1985 | Maiden | 356/409 |
| 4,535,241 | 8/1985 | Eberhardt | 250/339 |
| 4,578,762 | 3/1986 | Wong | 250/343 |
| 4,594,511 | 6/1986 | Cooper et al. | 250/339 |
| 4,707,133 | 11/1987 | Roberts et al. | 250/573 |

FOREIGN PATENT DOCUMENTS

| | | | |
|---|---|---|---|
| 3506372 | 8/1986 | Fed. Rep. of Germany | 250/343 |
| 0114438 | 7/1984 | Japan | 250/343 |

OTHER PUBLICATIONS

Non Linear Circuits Handbook, pp. 129-135; by The Engineering Staff of Analog Devices, Inc.; Edited by Daniel H. Sheingold; pub. by Analong Devices, Inc. Special Purpose Applications and Functions Circiuts; pp. 267-270.
Lock—In Amplifier, Models 120 and 122, §7.2.1.
Solomon—"A Reliable Accurate $CO_2$ Analyzer for Medical Use"—Hewlett—Packard Journal, Sep. 1981—pp. 3-21.

Primary Examiner—Janice A. Howell
Assistant Examiner—William F. Rauchholz
Attorney, Agent, or Firm—Willian Brinks Olds Hofer Gilson & Lione

[57] ABSTRACT

A non-dispersive infrared gas analyzer of the type typically used to measure concentrations of gases in medical and industrial applications has no moving parts and employs two or more miniature infrared sources ("microsources") which are electrical current-modulated to produce modulated infrared radiation for synchronous detection. The microsources are operated at different frequencies. The frequency-multiplexed detector signal is demodulated and ratioed to yield an output which is correlated to the gas concentration in the sampler chamber.

23 Claims, 12 Drawing Sheets

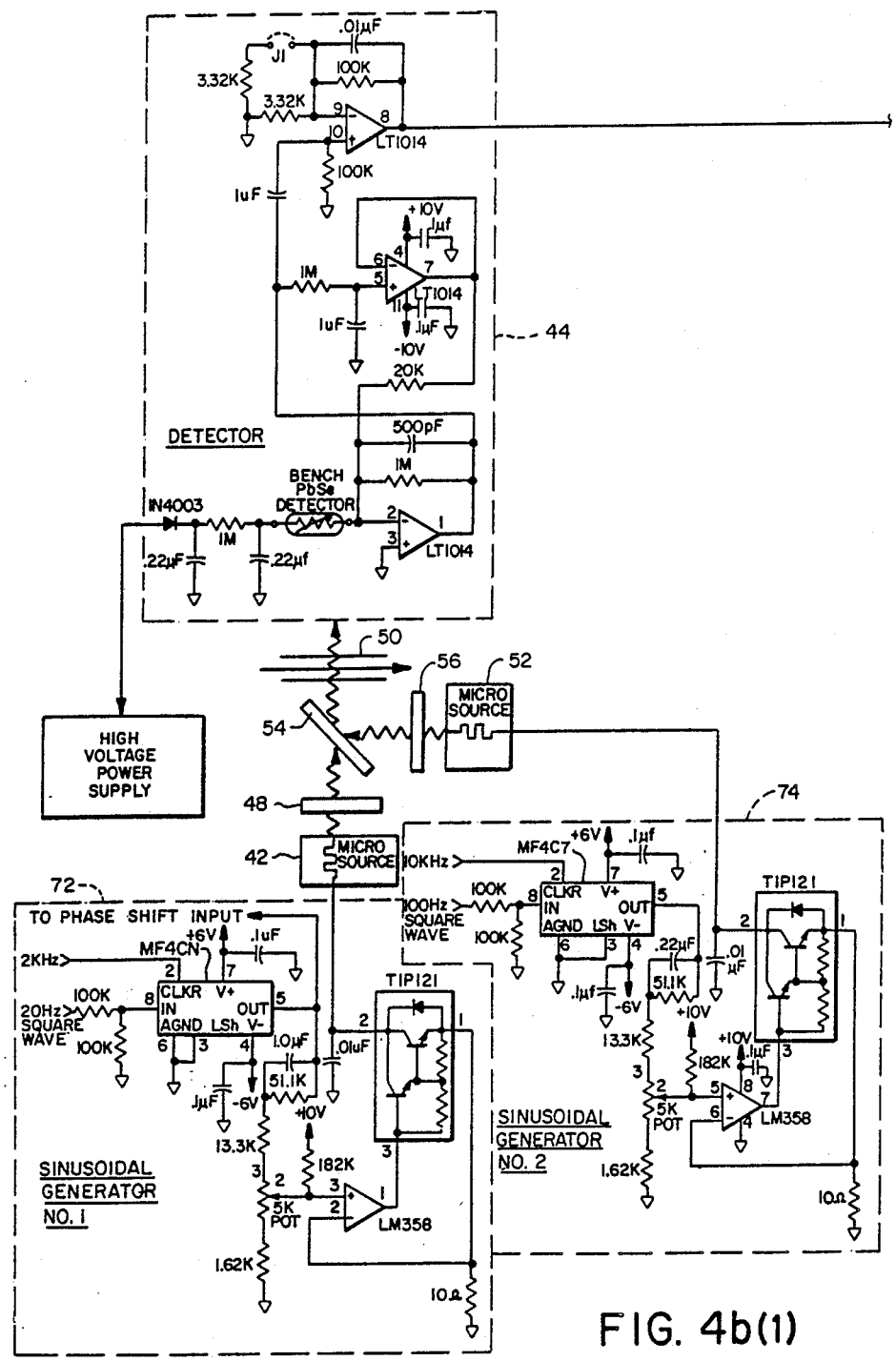
FIG. 4b(1)

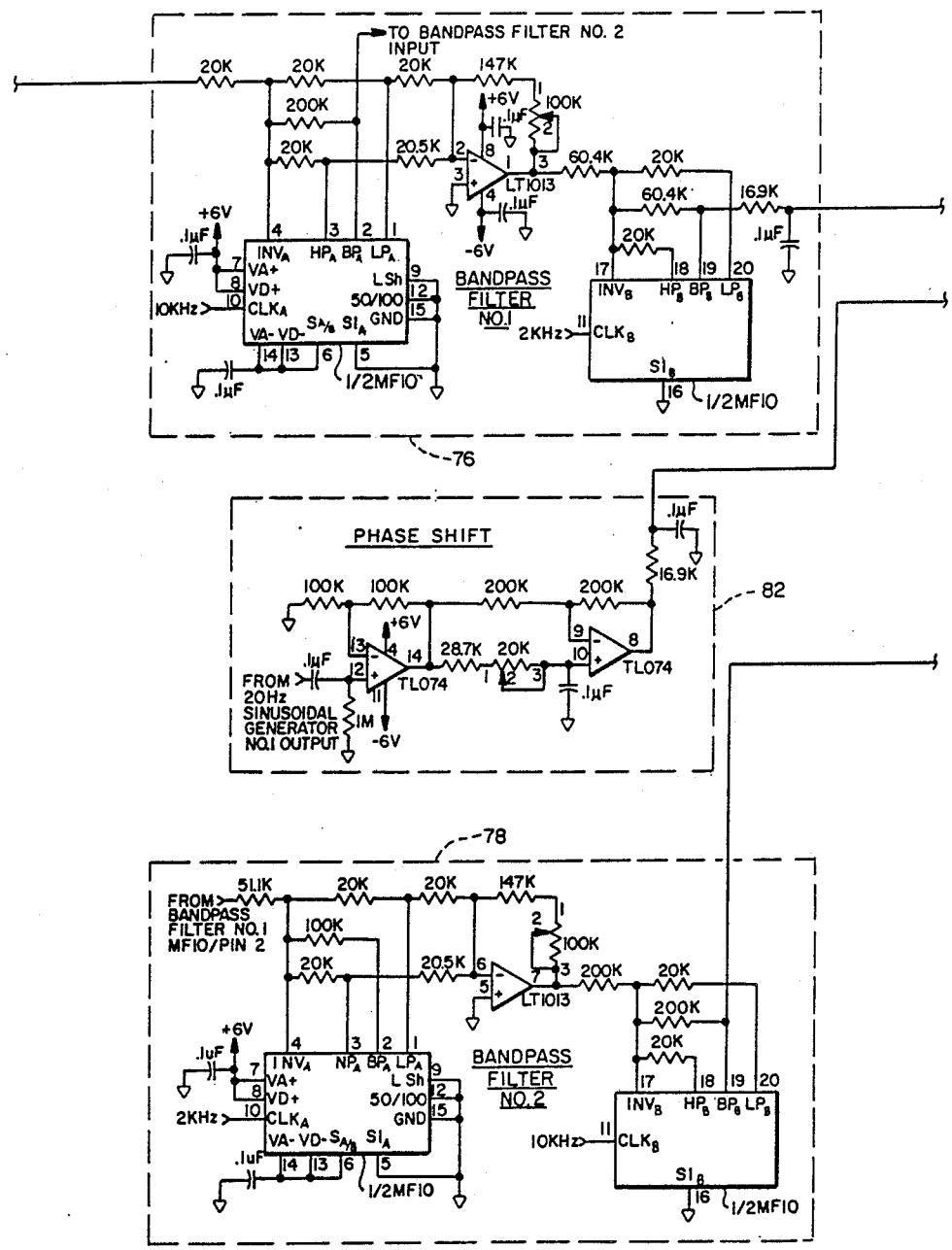
FIG. 4b(2)

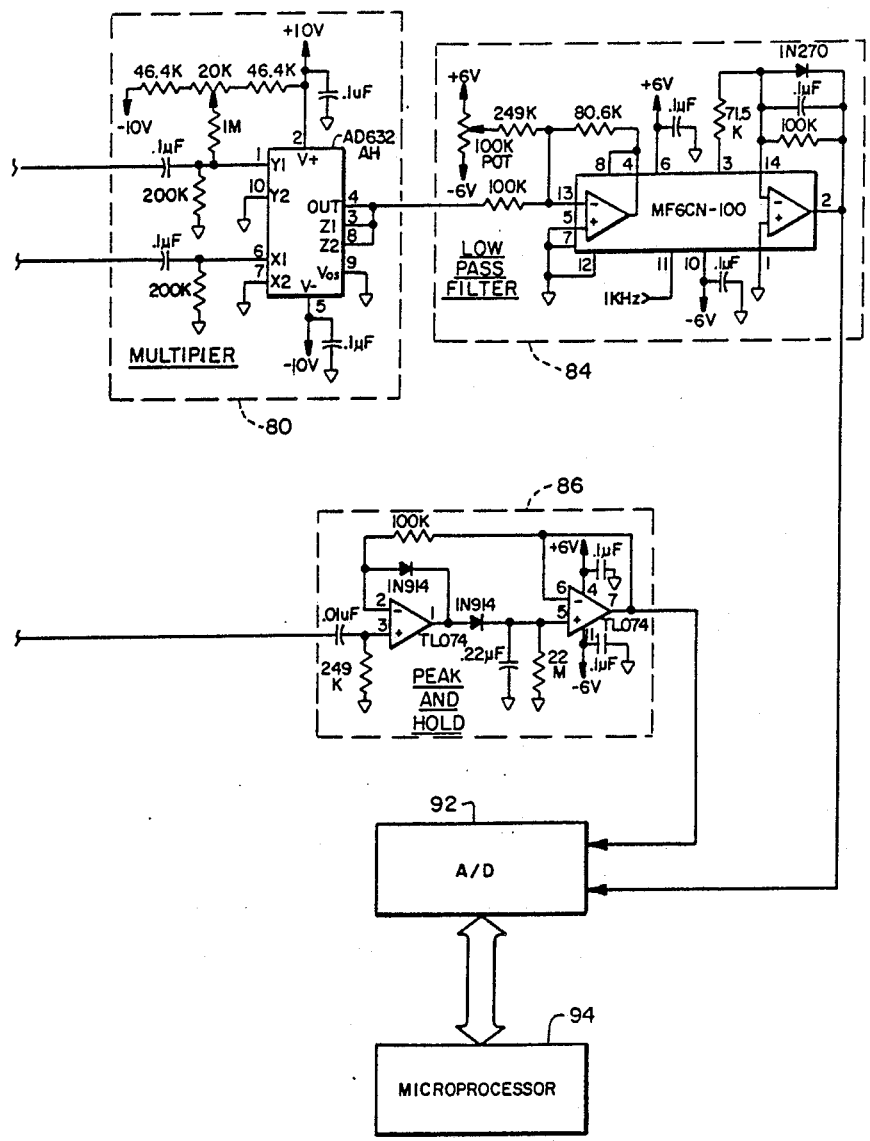
FIG. 4b(3)

SOLID STATE NON-DISPERSIVE IR ANALYZER USING ELECTRICAL CURRENT-MODULATED MICROSOURCES

BACKGROUND OF THE INVENTION

1. Technical Field

This invention relates to the quantitative measurement of the concentration of a particular gas in a gas mixture using the principle of non-dispersive infrared absorption. This invention provides an apparatus for such measurements which in the preferred embodiment includes two or more electrical current-modulated infrared microsources. These microsources eliminate the need for a conventional mechanical chopper for the synchronous detection of infrared radiation and render the gas analyzer completely solid-state with no mechanical moving parts. The low electrical power requirements of the apparatus allow for battery operation.

BACKGROUND OF THE INVENTION

This invention will be described as applied to an apparatus for the measurement of carbon dioxide gas ($CO_2$) Such measurement apparatus is generally referred to as a gas analyzer and will be described as a carbon dioxide sensor. The non-dispersive infrared technique utilizing the 4.26 micron absorption band of $CO_2$ has been widely used in the gas analyzer industry for the detection of $CO_2$. The term "non-dispersive" as used herein refers to the use of devices such as narrow band-pass filters instead of prisms or diffraction gratings to isolate for purposes of measurement radiation at 4.26 micron that coincides with a strong absorption band in the infrared absorption spectrum of the $CO_2$ gas. This technique offers a number of advantages including speed of response and greater sensitivity over older methods that use the principle of heat transfer based upon radiation absorption by $CO_2$.

The measurement of carbon dioxide gas concentration in nearly all of the gas analyzers available commercially today uses an infrared absorption technique. Carbon dioxide is made up of poly-atomic molecules that absorb infrared radiation within specific wavelength bands, including the 4.26 micron absorption band mentioned above. In the simplest type of measurement apparatus, known as the "single-beam" configuration, the isolated 4.26 micron radiation from an infrared source is made to traverse a sample chamber containing $CO_2$ or a mixture of $CO_2$ with other gases such as nitrogen and is partially absorbed, thus decreasing the incident radiation on an infrared detector. This intensity decrease is related to the number of $CO_2$ molecules present in the gas mixture and can be directly correlated to the $CO_2$ partial pressure ($pCO_2$) Patents such as Passaro U.S. Pat. No. 4,423,739, Burough U.S. Pat. No. 4,200,791, McClatchie U.S. Pat. No. 4,013,260, and Takami U.S. Pat. No. 3,893,770 disclose single beam systems which use conventional infrared sources.

In practice the single-beam configuration is rarely used in commercial $CO_2$ gas analyzers due to output drifts caused by temperature and aging instabilities of components such as the infrared source, filter and detector. Instead a "double-beam" configuration is normally used to provide an additional reference path (hence double-beam) where no $CO_2$ absorption takes place. A ratio is then established between the detector output for the sample path and the detector output for the reference path to determine the $CO_2$ gas concentration in the sample path. This double-beam approach satisfactorily eliminates the output drifts caused by environmental and temporal changes of component characteristics that plague the single-beam configuration.

The most common double-beam configuration utilizes a single source. Using spherical mirrors, infrared radiation from this source is first collimated and then refocussed onto a single detector after traversing a mechanical chopper and either the sample chamber or the reference chamber. Isolation of the 4.26 micron radiation is achieved via a narrow band-pass filter placed in front of the detector, which can for example be a PbSe photoconductor. The reference chamber does not contain any gases such as $CO_2$ which absorb the 4.26 micron radiation. The mechanical chopper provides slots in its blade which alternately send the collimated radiation from the source through the sample and the reference chambers. Thus, the mechanical chopper not only provides the means for synchronous detection of relevant radiation but also creates sample and reference detector signals, whose ratio is used to determine the $CO_2$ gas concentration in the sample chamber.

In another implementation of the double-beam configuration discussed in Blau, Jr. U.S. Pat. No. 3,811,776, a non-dispersive gas analyzer incorporates, in addition to the narrow band-pass filter, a gas cell containing the gas of interest such as $CO_2$, and an identical cell evacuated or filled with a gas that is transparent at the wavelength used (4.26 micron for $CO_2$ gas). These cells alternately are moved into and out of a radiation beam. When a sample chamber is also placed in series with these cells, the alternate introduction of the absorbing and non-absorbing cells into the radiation beam creates a reference (absorbing cell) and a sample (non-absorbing cell) detector signal whose ratio is used to determine the $CO_2$ gas concentration in the sample chamber. Unlike the first double-beam configuration discussed earlier which utilizes two spatially distinct radiation paths, the Blau configuration uses only one common radiation path but takes advantage of the principle of non-linear absorption by the gas ($CO_2$) to be measured as discussed in Wong U.S. Pat. No. 4,578,762 in order to create the reference and sample signals.

Typically, both the switching of the beams as discussed in the first double-beam configuration and the alternative movement of the cells as discussed in the second double-beam configuration above are accomplished by rotating machinery. Grant U.S. Pat. No. 4,489,239, Kreuzer U.S. Pat. No. 4,044,257, and Ishida U.S. Pat. No. 3,898,462 disclose other double beam gas analyzers which rely on rotating mechanical chopper wheels. The use of such rotating machinery has often been considered necessary but undesirable. Typical problems include noise, vibration, size, weight, electrical noise from the driving motor, and wear of the bearings. Also, commercially available gas analyzers today, such as carbon dioxide gas analyzers, often use a high power but inefficient infrared source whose dimensions are generally compatible with the bulky size of the basic mechanical chopper. Because of the size of the sensors themselves, many present day gas analyzers can only sample gases via a suctioning technique. In this technique, a built-in suctioning pump which resides inside the instrument is used to draw the gas into and out of the sample chamber for the concentration measurement. This technique has a number of drawbacks when compared with the more preferred "flow-through" or "on-airway" sampling technique. The most prominent drawbacks are the clogging of the sampling line and the distortion of the gas concentration profile due to diffusion. The latter is a common problem in view of the relatively long sampling line that is required and the finite flow rate of the gas through the sampling line.

Although some gas analyzers, most notably the Hewlett-Packard capnometer (Solomon, "A Reliable Accuate CO2 Analyzer for Medical Use", Hewlett Packard Journal, Sept. 1981, pp. 3–21) manage to replace the bulky mechanical choppers with novel miniature electromagnetic rotation wheels for the purpose of beam switching, some serious problems still persist. The most notable ones are reliability against rough handling such as dropping of the sensor on the floor during routine use and the wear and tear of the mechanical bearings.

Despite the fact that these latest analyzers use much smaller sensors to the extent that flow-through or on-airway sensing is achieved, as long as mechanical moving parts are used, the problems discussed above still exist.

In the past, a number of optical systems have been proposed which utilize IR sources that are modulated by modulating the electrical current which drives the IR source. Aargard U.S. Pat. No. 4,322,621 discloses a dual beam system which employs IR LED's that are driven with square wave signals. LED's provide the disadvantage that the available light frequencies that can be obtained are limited and may not be suitable for all applications. Eberhardt U.S. Pat. No. 4,535,241 discloses a dual beam system which uses modulated lasers which eliminate the need for a mechanical chopper and Ophoff U.S. Pat. No. 4,437,005 and Maiden U.S. Pat. No. 4,500,207 disclose single beam systems which use electrically modulated broad band thermal IR sources. As explained above, such single beam systems suffer from severe disadvantages associated with time variations of the source and the optical components of the system.

The present inventors recognized that the problems associated with the rotating machinery, lasers, and LED's of prior art gas analyzers can be overcome by employing solid-state devices to accomplish the desired switching action of broad band infrared sources for the double-beam measurement configuration, thereby making possible a simplified gas analyzer having no moving parts. The present inventors further recognized that the use of a pair of electrical current-modulated microsources combined with a dual-frequency synchronous detection scheme can provide a high performance miniature solid-state infrared gas sensor for gases such as carbon dioxide.

SUMMARY OF THE INVENTION

One object of the present invention is to provide a small, compact, non-moving apparatus for effectively producing two radiation paths, one reference and one sample, for the synchronous detection of carbon dioxide or other gases using the non-dispersive infrared technique. Another object is to improve the response time of a gas analyzer which incorporates modulated thermal IR sources.

The invention itself is defined by the following claims. The preferred embodiments described below combine two converging or focussed radiation beams from two broad band infrared microsources positioned 90° from each other onto a common photodetector using a 45° inclined silicon beam splitter.

A narrow band-pass filter which passes radiation of wavelength coincident spectrally with an absorption band of the gas whose concentration is to be measured is placed in front of one microsource. This defines the "sample" beam. Another narrow band-pass filter which passes radiation of wavelength non-coincident spectrally with any absorption bands of commonly known gases including the gas of interest is placed in front of the other microsource. This defines the "reference" beam. A sample chamber such as a cell or an airway is interposed between the beam splitter and the photodetector.

In accordance with one preferred embodiment of the present invention, the microsources are electrically modulated at two distinct and high-multiple frequencies (e.g., at a ratio of 4:7) by passing modulated electrical currents through them. The frequency-multiplexed signal at the photodetector is demodulated to recover the signal amplitudes belonging to each of the two channels (sample and reference). The ratio of the sample signal over the reference signal is correlated with the amount of gas in the sample chamber for the concentration measurement. In certain forms of this embodiment, the sample signal is combined with another periodic signal to improve the response time of the system in detecting changes in amplitude of the sample signal.

In accordance with an alternative embodiment, the microsources are sequentially pulsed at the same frequency by passing modulated electrical currents through them. The time-multiplexed signal at the photodetector is gated with proper delay times for sampling both the reference and the sample signal levels. The ratio of the sample signal over the reference signal is correlated with the amount of gas in the sample chamber.

The invention itself, together with further objects and attendant advantages, will best be understood by reference to the following detailed description, taken in conjunction with the accompanying drawings.

BRIEF DESCRIPTION OF THE DRAWINGS

FIG. 4b(1)–4b(3) show a detailed electrical schematic diagram of a circuit which implements the block diagram of FIG. 4a.

FIG. 6(a) is an electrical current drive waveform for pulsing the signal microsource at frequency $f_1$.

FIG. 6(b) is the output waveform from the detector due to the signal microsource if the latter were to operate alone.

FIG. 6(c) is an electrical current drive waveform for pulsing the reference microsource at frequency $f_2$.

FIG. 6(d) is the output waveform from the detector due to the reference microsource if the latter were to operate alone.

FIG. 6(e) is a frequency-multiplexed output waveform from the detector due to both the signal and reference microsources operating simultaneously.

FIG. 8(a) is an electrical current drive waveform for pulsing the signal microsource at frequency f.

FIG. 8(b) is the output waveform from the detector due to the signal microsource if the latter were to operate alone.

FIG. 8(c) is an electrical current drive waveform for pulsing the reference microsource at frequency f.

FIG. 8(d) is the output waveform from the detector due to the reference microsource if the latter were to operate alone.

FIG. 8(e) is the output waveform from the detector due to both the signal and the reference microsources operating sequentially at frequency f.

FIG. 8(f) is the sampling pulse for measuring the detector output level during the signal period of illumination.

FIG. 8(g) is the sampling pulse for measuring the detector output level during the reference period of illumination.

DETAILED DESCRIPTION OF THE PRESENTLY PREFERRED EMBODIMENTS

Figure 1:
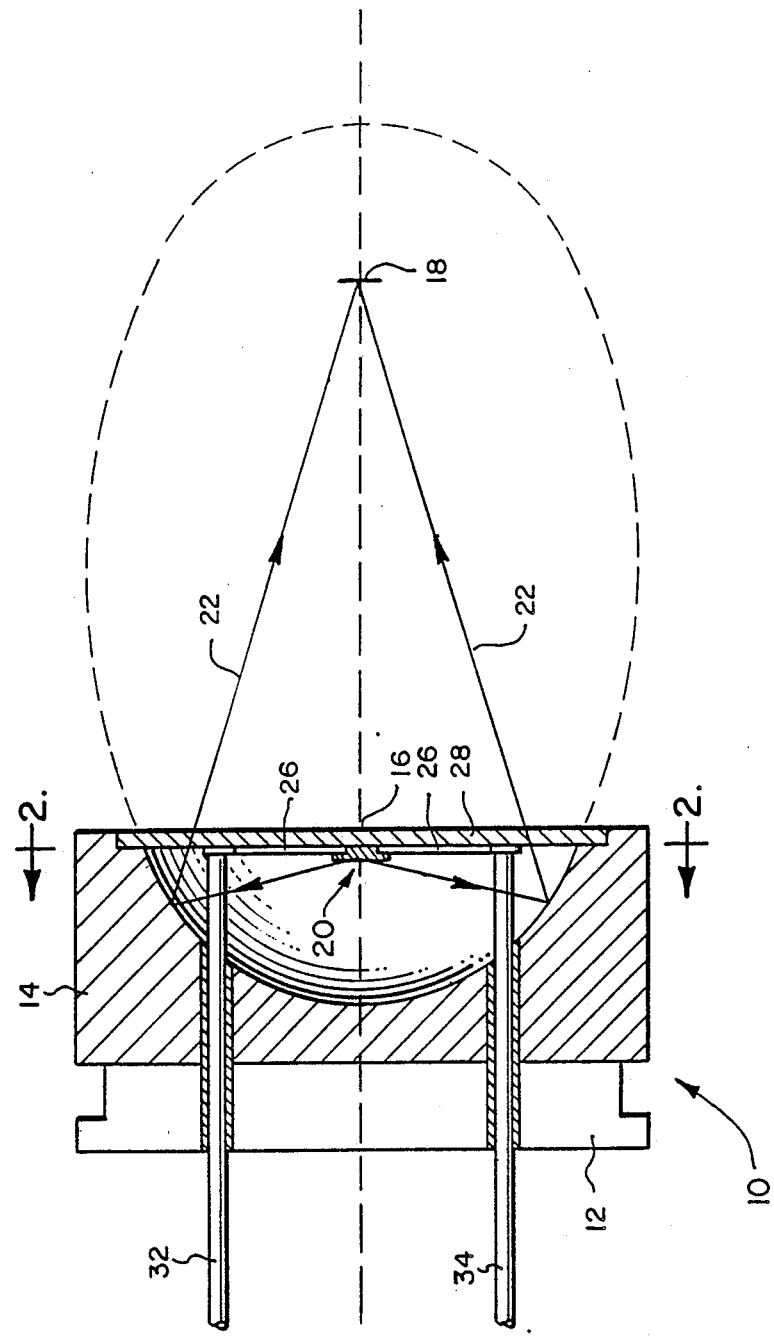
FIG. 1 is a schematic diagram of a miniature infrared source ("microsource") which is used in the preferred embodiments described below to generate modulated infrared radiation.
Figure 2:
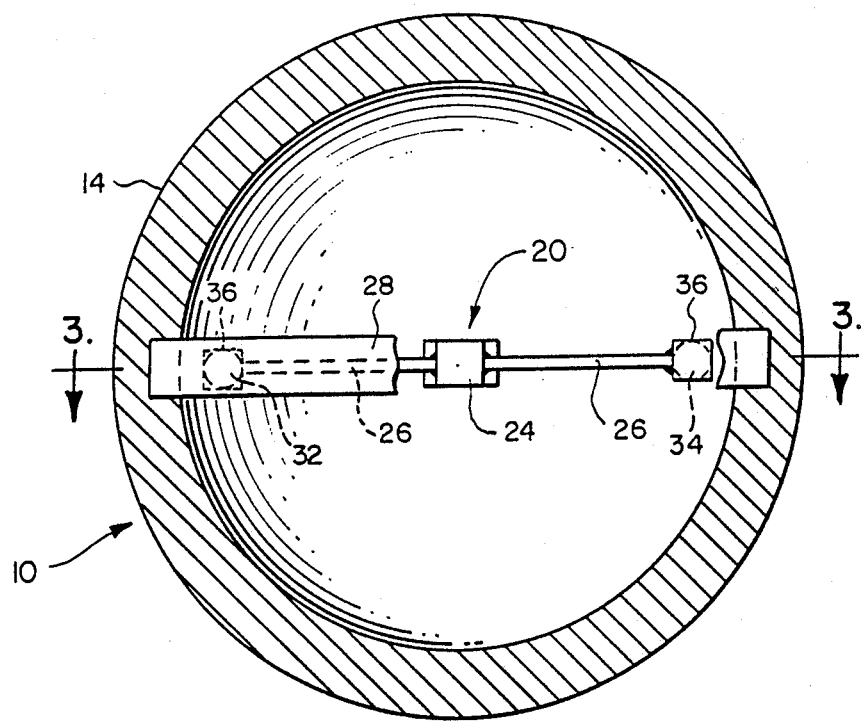
FIG. 2 is a sectional view taken along line 2—2 of FIG. 1.
Figure 3:
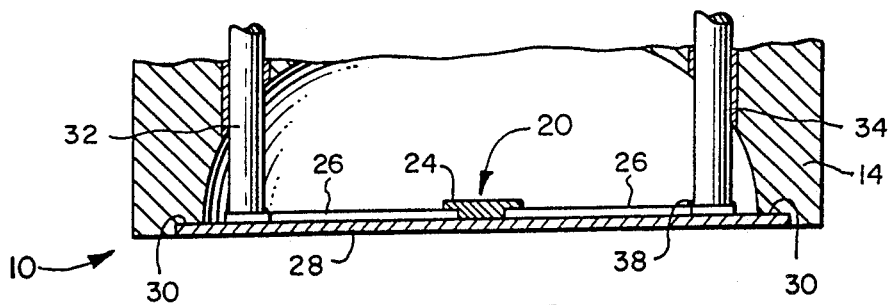
FIG. 3 is a sectional view taken along line 3—3 of FIG. 2.

The preferred embodiments of the present invention use miniature infrared sources (hereafter known as "microsources") which can be driven with modulated electrical current to produce modulated infrared radiation for synchronous detection. FIG. 1 shows the presently preferred embodiment of the microsource 10. The microsource includes a header 12 which supports an ellipsoidal mirror 14. The conjugate foci 16 and 18 of the ellipse act as the object (16) and the image (18) points, respectively. As shown in FIG. 1, the microsource 10 includes a heating element 20 positioned at the object point to emit radiation 22 that is focused by the mirror 14 to the image point. As shown in FIGS. 2 and 3, the heating element 20 comprises a thick film resistor pad 24 (typically 100 ohms per square) contacted on both sides by a thick film gold electrode 26, all deposited on a thermally and electrically insulating alumina substrate 28. Each of the electrodes 26 defines a respective conductive pad 36. The heating element 20 is supported diametrically across the ellipsoidal mirror 14 in recesses 30 as depicted in FIG. 3. Leads 32, 34 of the header 12 provide electrical interconnections to the heating element 20 through contacts to the conductive pads 36 as shown in FIG. 3. The leads 32, 34 of the header 12 also serve to hold the heating element 20 mechanically in place via solder joints 38.

With reference to FIG. 2, when electrical current I is made to pass from one lead 32 to the other lead 34 across the heating element 20, the resistor pad 24 with resistance R heats up rapidly according to the $I^2R$ law of ohmic heating. When the current I is reduced, the resistor pad 24 cools down via a combination of conductive heat loss through the substrate 28 and convective heat loss through the ambient gas contacting the resistor pad 24 and the nearby surfaces. By proper choice of materials the resistor pad 24 can be made to heat up and cool down rapidly as the electrical current passing through it is modulated. The microsource distributed by Hibshman Corporation of San Luis Obispo California as Model A30R has been found suitable for use in this embodiment. This microsource can be pulsed at frequencies up to 2 KHz and its peak-to-peak (AC) output has been shown to be stable to within one part in $10^3$ for prolonged periods of time both in continuous and intermittent operation. Mean life to failure for the microsource when pulsed continuously at 100 Hz with a 20% duty factor is in excess of 10,000 hours.

Figure 4:
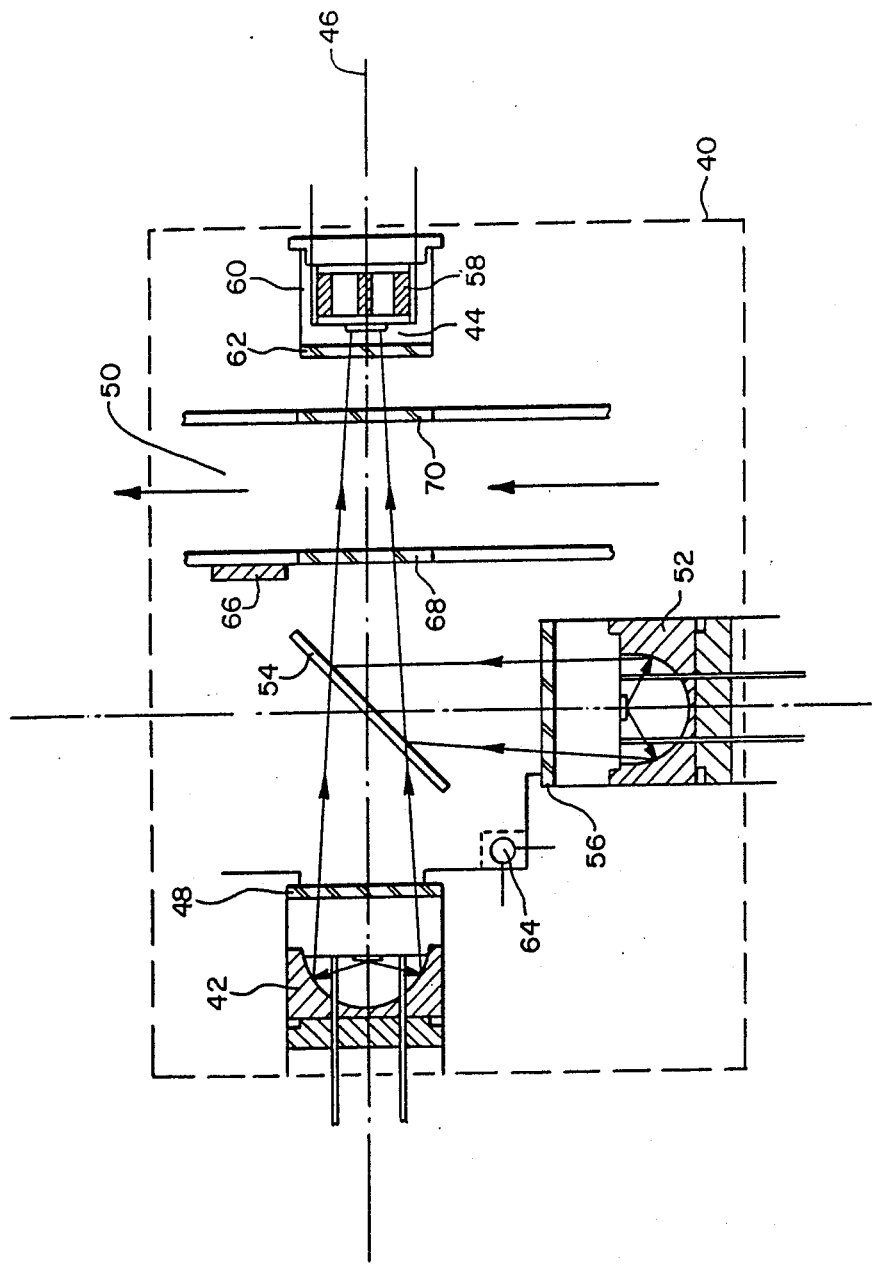
FIG. 4 is an optical diagram showing the optical system of a preferred embodiment of a carbon dioxide sensor in accordance with this invention.

FIG. 4 shows the optical system of a preferred embodiment 40 of a carbon dioxide sensor in accordance with the present invention. In the configuration shown, a first microsource 42 is provided which is equipped with an ellipsoidal mirror for focussing the emitted infrared radiation onto a photodetector 44 (such as a PbSe photoconductor) along optical axis 46. A narrow band-pass filter 48 having its center frequency coincident with the 4.26 micron absorption band of $CO_2$ is placed in front of the microsource 42 to pass the "sample" radiation beam through the sample chamber 50 onto the detector 44. A second microsource 52 also equipped with a focussing ellipsoidal mirror is oriented at 90° to the optical axis 46 such that a silicon beam splitter 54 oriented at 45° to the optical axis 46 directs radiation from microsource 52 also onto the same detector 44. The sample chamber 50 can be an airway or a cell. A narrow band-pass filter 56 having its center frequency non-coincident with the absorption bands of all common gases including $CO_2$ (e.g., at 3.6 micron) is placed in front of the microsource 52.

The beam splitter 54 does not affect the focussing of the radiation from the microsource 42 but does reflect approximately 50% of the radiation output from the microsource 42 at 90° from the optical axis 46 and away from the detector 44. The same is true for approximately 50% of the radiation emanating from the microsource 52. The 45° placement of the beam splitter 54 ensures that both radiation beams (the "sample" and the "reference" from microsources 42 and 52, respectively) are coincident through the sample chamber 50 before reaching the detector 44. Preferably the two microsources 42, 52 are equidistant from the beam splitter 54.

In order to improve the signal-to-noise ratio of the overall optical system, the detector 44 is mounted onto a single-stage thermoelectric (TE) cooler 58 and is encapsulated in a hermetic environment of dry $N_2$ by a cannister 60 equipped with its own sapphire window 62. Since the microsources 42, 52, the narrow band-pass filters 48, 56, the silicon beam splitter 54, and the detector 44 are all temperature sensitive, they are mounted on a common heat sink structure 40 made out of a thermally conductive material such as aluminum, as depicted schematically in FIG. 4. Furthermore, the temperature of the structure 40 is regulated with the help of a thermistor 64 and a power transistor 66.

Since the microsources 42, 52 and the hot side of the TE cooler 58 are all heat generators, the power transistor 66 needs to be turned on only in the rare instances of a cold ambience. When the temperature reaches about 37° C with the power transistor shut off, heat is dumped to the external ambience via the casing (not shown in FIG. 4).

The temperature regulation of the heat sink structure 40 to about 37° C. also helps to keep the sample chamber windows 68 and 70 free from any moisture condensation. This is especially important when the carbon dioxide sensor is used in a "flow-through" or "on-airway" sampling mode. The temperature of expired air from a person is close to 37° C. when measured near the mouth and if the temperature of the windows is below the expired air temperature, moisture will condense on the windows leading to a significant drop in the available signal for $CO_2$ measurement.

Figure 4A:
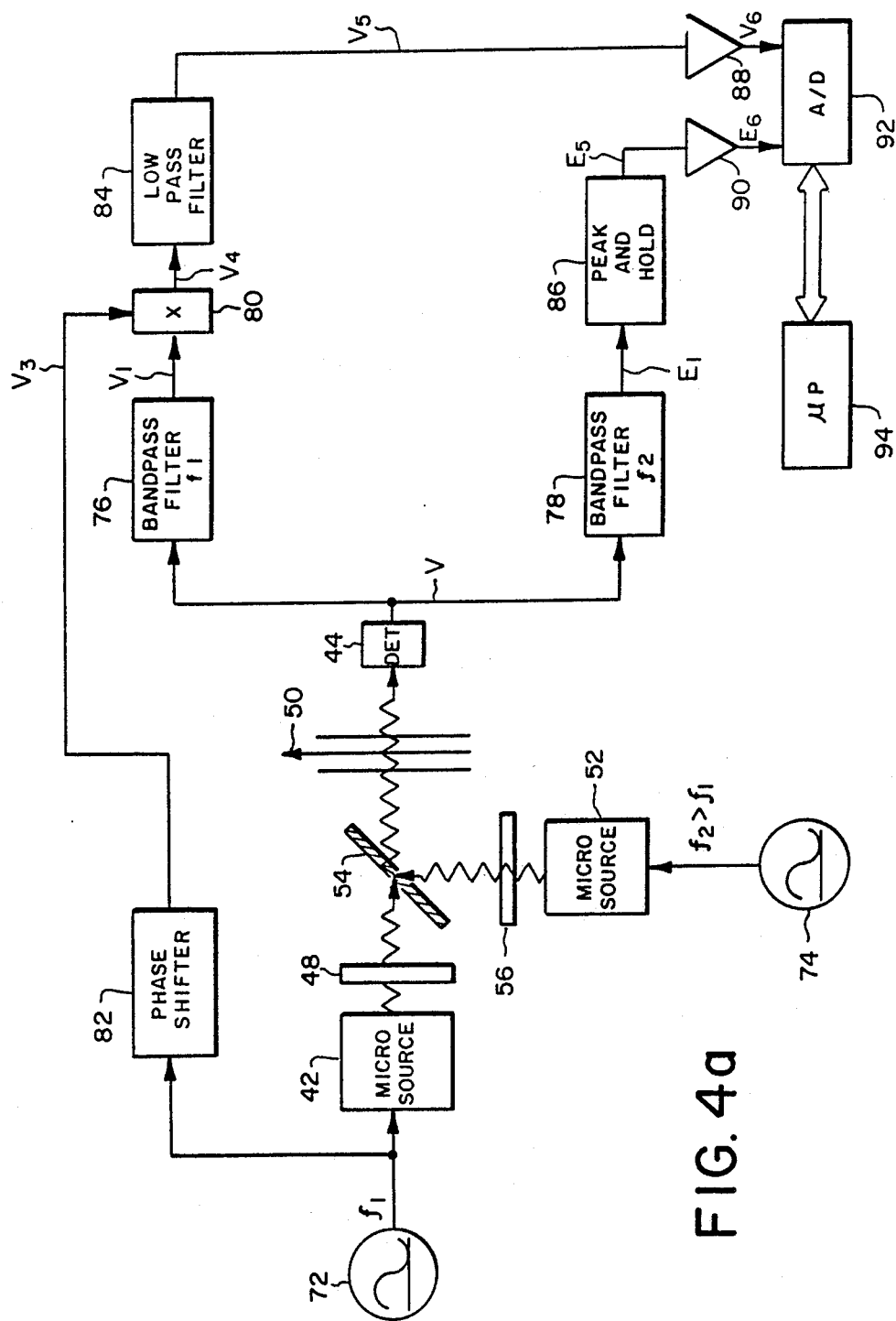
FIG. 4a is an electronic block diagram showing the electronic system used in the preferred embodiment of FIG. 4.

The carbon dioxide sensor optical system depicted schematically in FIG. 4 is preferably used with the electronic system shown in block diagram form in FIG. 4a. Microsources 42 and 52 are driven by signal generators 72 and 74 at frequencies $f_1$ and $f_2$, respectively, which are relatively high multiples of each other, e.g., $5f_1 = f_2$ and the modulation signal is of the form:

$$S_j = K_j(1 + \sin 2\pi f_j t),$$

where $j = 1$ to 2, $K_j$ is the amplitude coefficient, and $K_j$ represents a 100% modulation level, that is, $0 \leq S_j \leq 2K_j$. The amplitude of emitted radiation $I_j$ emanating from each microsource 42, 52 will not, however, be of the same form as $S_j$, since the increase in source temperature is directly related to the square of $S_j$ (electrical power) and the source radiation is directly related to the fourth power of the source absolute temperature. However, the amplitude $A_j$ of the fundamental harmonic of the AC component of $I_j$ ($I_{jac} = A_j \sin 2\pi f_j t$) provides a useful means of conveying the pertinent information while eliminating DC drift and the low frequency noise of the detector and source. Due to the thermal time-constants of the microsources 42, 52, the amplitude $A_j$ declines rapidly as $f_j$ increases such that $A_j$ (100 Hz)/$A_j$(10 Hz) = 0.1. The most useful range of frequency in the present embodiment is less than 120 Hz. The time-varying radiation emanating from the microsource 42 passes through narrow band-pass filter 48 with center frequency $\lambda_1$, the silicon beam splitter 54, and the sample chamber 50 before striking the detector 44. The center wavelength $\lambda_1$ of the band-pass filter 48 coincides with the 4.26 micron absorption band of $CO_2$ and the radiation path from the microsource 42 constitutes the "sample beam" of the $CO_2$ sensor Similarly, radiation emanating from the microsource 52 passes through the narrow band-pass filter 56 with center frequency $\lambda_2$, reflects off the silicon beam splitter 54, and passes through the sample chamber 50 before striking the detector 44. The center wavelength $\lambda_2$ of the bypass filter 56 is non-coincident with the absorption bands of all common gases including $CO_2$ and can for example be at 3.6 micron. The radiation path from the microsource 52 constitutes the "reference beam" of the $CO_2$ sensor The amplitude of the "sample beam" at frequency $f_1$ decreases as a function of increasing $CO_2$ gas concentration in the sample chamber whereas the "reference beam" amplitude at frequency $f_2$ is not affected and remains substantially constant.

The frequency multiplexed signal made up of the sample beam and the reference beam received at the detector 44 is routed to narrow band-pass filters 76 and 78 with center frequencies of $f_1$ and $f_2$, respectively, as shown in FIG. 4a. The outputs of the filters 76, 78 are of the form:

$$V_1 = A_1(t) \sin 2\pi f_1 t,$$

$$E_1 = A_2 \sin 2\pi f_2 t.$$

Since it is an object of this invention to provide clinically meaningful, breath-by-breath, $CO_2$ waveforms (capnograms) the system preferably exhibits a rapid response time (time constant less than 0.1 sec.) in conjunction with a sufficiently high signal-to-noise ratio (S/N greater than 50:1). To maximize the S/N ratio, the "sample beam" modulation frequency $f_1$ should be as low as possible to overcome the AC amplitude attenuation attendant with the thermal response characteristics of the microsources 42, 52, and high enough to provide the desired rapid response characteristics. The pertinent $CO_2$ information is carried by the time-varying amplitude coefficient $A_1(t)$ of the sinusoidal waveform $V_1$ Sampling the positive and negative peak values of $V_1$ would provide a sampling rate of $2f_1$ and a marginal time resolution for the reconstruction of a smooth $CO_2$ waveform This embodiment provides a means for continously monitoring $A_1(t)$ without discrete sampling. This has been implemented by using the following trigonometric identity:

$$A_1(t) \sin x \cdot A_3 \sin x = A_1(t) \cdot A_3 (1 - \cos 2x)/2,$$

where $x = 2\pi f_1 t$. This nonlinear operation provides a low frequency component, $(A_3/2)A_1(t)$, while shifting the AC carrier component to a frequency of $2f_1$. An analog multiplier 80 is used to obtain the product $V_4$ from signals $V_1$ and $V_3$, where $V_3$ is equal to $A_3 \sin 2\pi f_1 t$ and is obtained from the sinusoidal waveform generator 72 after phase alignment with $V_1$ by phase shifter 82 and AC coupling to remove the DC component. A low-pass filter 84 is used to isolate the low frequency component, $V_5$, by eliminating the $2f_1$ AC component.

The lower amplitude, higher frequency, "reference beam" signal $E_1$ carries information which changes very gradually, and the magnitude of $A_2$ is obtained by discrete sampling of the peak values by the peak/hold circuitry 86. After signal conditioning by amplifiers 88 and 90, respectively, the signals containing $A_1$ and $A_2$ information, $V_6$ and $E_6$, are digitized by an A/D convertor 92 and the $CO_2$ concentration is obtained via digital computation performed by a microprocessor 94.

Since the amplitudes of the AC carrier components are proportional to the amplitudes of the AC radiation I emanating from each microsource 42 and 52, the output voltages $V_6$ and $E_6$ are linearly related to the AC radiation amplitudes $I_1$, $I_2$, as follows:

$$v_j = b_j \times I_j + a_j.$$

Where $j = 1$ refers to the sample signal $V_6$, $j = 2$ refers to the reference signal, $E_6$, $v_1 = V_6$, $v_2 = E_6$, $a_j$ is a DC component due to offset voltage in the analog section, and $b_j$ is the proportionality constant relating $I_j$ to $v_j$. To correct for differences between the two microsources 42, 52 as may occur with aging, the values for $a_j$ and $b_j$ are updated from time to time. For this purpose the ratio of the reference to sample beam intensities will be assigned to unity when C, the concentration of $CO_2$ in the sample cell, is equal to zero, that is:

$$I_1/I_2 = 1 \text{ when } C = 0.$$

Two steps are required to obtain the parameter values. Firstly, $I_j$ is set to zero by momentarily removing power from the microsources 42, 52 and measuring the outputs $v_j$ which are now equal to $a_j$. Secondly, with the microsources 42, 52 energized and C = 0, $b_j$ values are calculated by setting $I_j$ to a value of 1, or $$b_j = v_j - a_j.$$ Thus, the normalized radiation intensity is given by:

$$I_j = (v_j - a_j)/b_j = 1 \text{ when } C = 0,$$

and since $I_1 = I_2 = 1$, then $I_1/I_2 = 1$.

The empirical relationship between the ratio $I_1/I_2$ and the $CO_2$ concentration, C, has the following form:

$$I_1/I_2 = K_1 \exp(-K_2 C) + K_3 \exp(-K_4 C) + K_5,$$

where $K_i$ are derived from a least square error fit of the plot of $I_1/I_2$ versus C.

In this embodiment the microprocessor 94 calculates the $CO_2$ concentration by using a look up table based on the above curve fit. FIGS. 4b(1) to 4b(3) provides a detailed electrical schematic diagram of a circuit which implements the block diagram of FIG. 4a.

Figure 5:
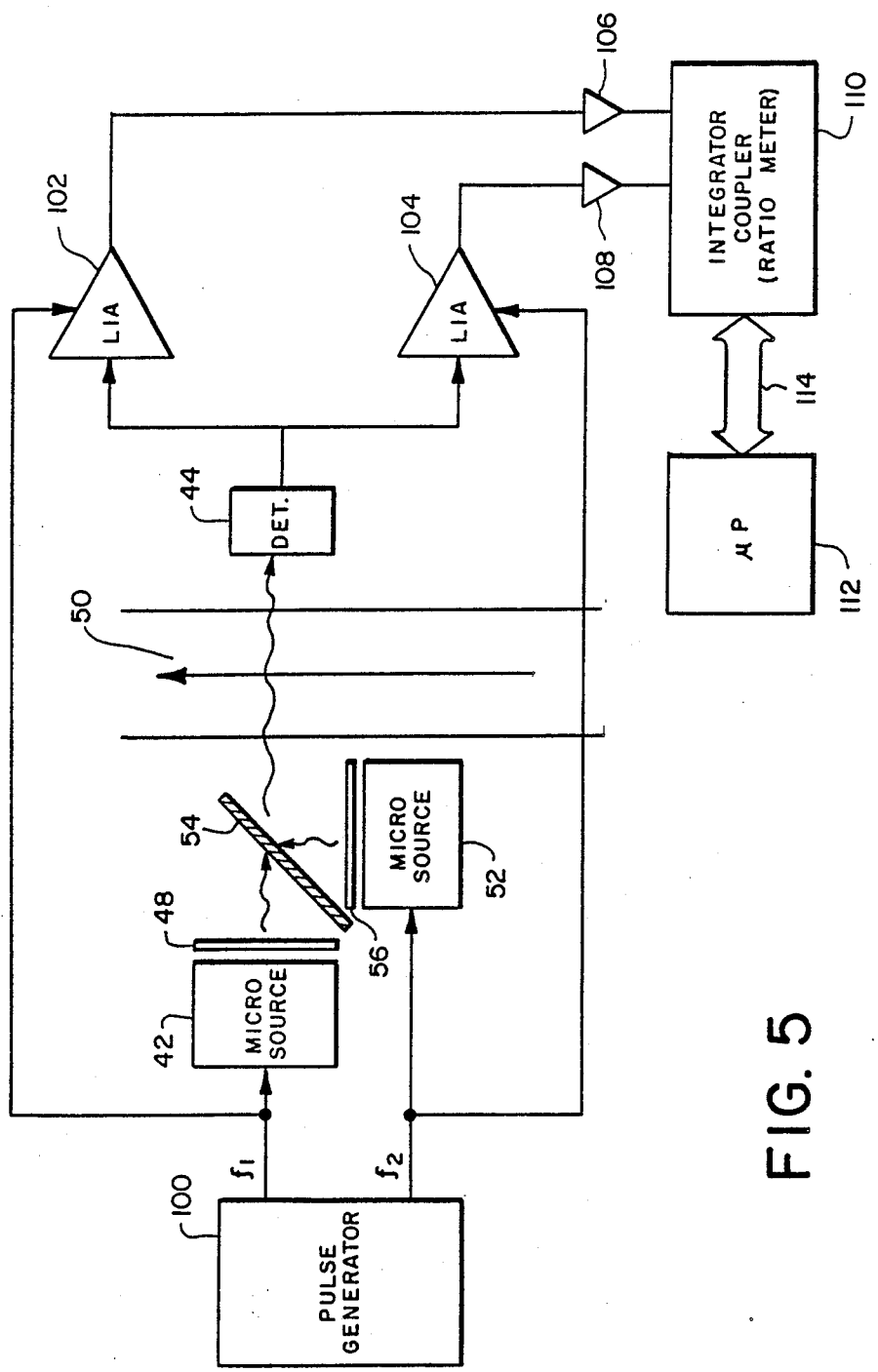
FIG. 5 is an electronic block diagram showing an alternate electronic system suitable for use in the embodiment of FIG. 4.

In another embodiment of the present invention, the optical system depicted schematically in FIG. 4 is used in conjunction with the electronic system shown in block diagram form in FIG. 5. Microsources 42, 52 are driven by a pulse generator 100 at frequencies $f_1$ and $f_2$, respectively, where $f_1$ and $f_2$ are relatively high multiples of each other, e.g., $7f_1 = 4f_2$ The optical elements of FIG. 5 are identical to those described above in connection with FIGS. 4 and 4a.

The frequency multiplexed signal received at the detector 44 is routed to lock-in amplifiers 102 and 104 as shown in FIG. 5. The lock-in amplifier 102 receives its reference frequency $f_1$ from the pulse generator 100 and extracts the $f_1$ component of the detector signal. The lock-in amplifier 104 also receives its reference frequency $f_2$ from the pulse generator 100 and extracts the $f_2$ component of the detector signal. After signal conditioning by amplifiers 106 and 108, respectively, the $f_1$ and $f_2$ components are fed into an integrator coupler (ratio meter) 110 for determining a ratio R which is equal to the amplitude of the $f_1$ component divided by the amplitude of the $f_2$ component. The ratio R can be calibrated to the concentration of $CO_2$ gas in the sample chamber 50. The output R from the integrator coupler 110 can be digitally transferred to a microprocessor 112 for further signal processing via a standard IEEE-488 interface 114 as shown in FIG. 5.

Figure 6A:
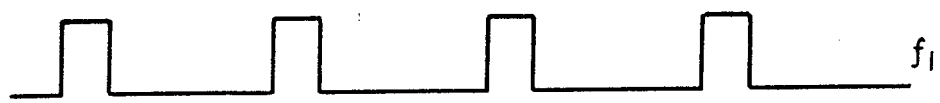
FIGS. 6(a)–6(e) are diagrams showing various electrical current drive and detector output signal waveforms pertaining to the electronic system of FIG. 5.
Figure 6B:
Figure 6C:
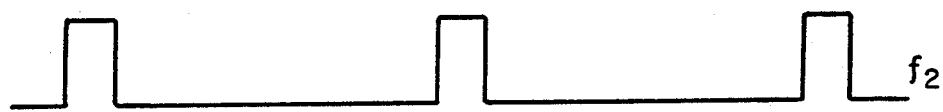
Figure 6D:
Figure 6E:

For the preferred embodiment of FIG. 5, the electrical current waveforms for driving the microsources 42 and 52 and the frequency-multiplexed output signal of the detector 44 are shown in FIGS. 6(a)–6(e). FIGS. 6(a) and 6(c) depict the current pulse waveforms for driving microsources 42 and 52 at frequencies $f_1$ and $f_2$, respectively, at a frequency ratio of 7:4. FIGS. 6(b) and 6(d) depict the respective detector output waveforms for radiation modulated at $f_1$ and $f_2$ if they were to arrive at the detector 44 individually and not frequency multiplexed. FIG. 6(e) shows the frequency multiplexed output of the detector 44 for the combined radiation modulated at $f_1$ and $f_2$ from microsources 42 and 52.

Figure 7:
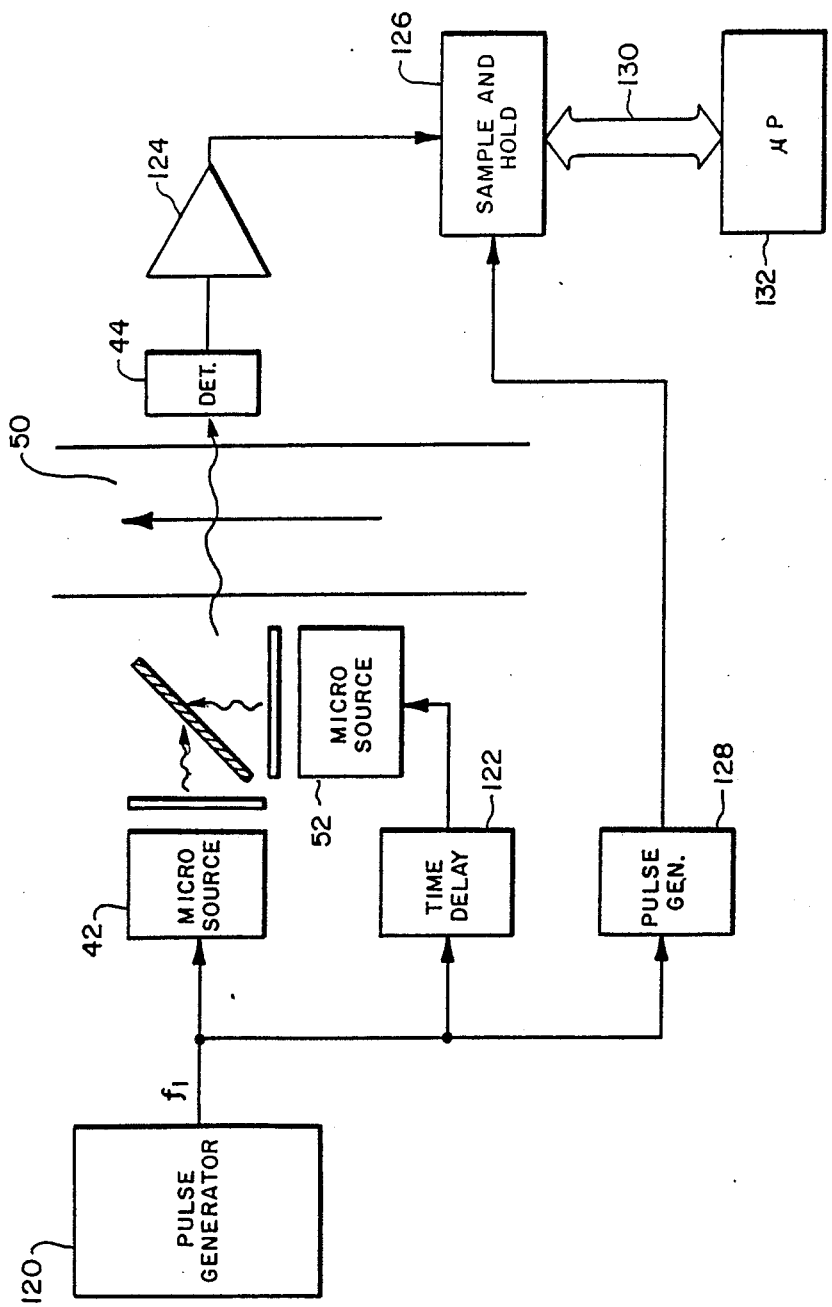
FIG. 7 is an electronic block diagram showing another alternate electronic system suitable for use in the embodiment of FIG. 4.
Figure 8A:
FIGS. 8(a)-8(g) are diagrams showing various electrical current drive, detector output signal and sampling waveforms pertaining to the electronic system of FIG. 7.
Figure 8B:
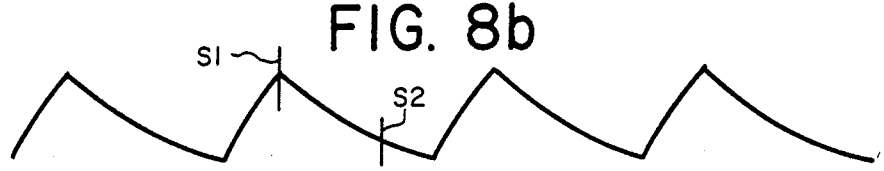
Figure 8C:
Figure 8D:

In a third preferred embodiment of the present invention, the optical system depicted schematically in FIG. 4 is used with the electronic system shown in block diagram form in FIG. 7. The microsources 42 and 52 are driven sequentially at the same frequency f and with a duty factor of 25% by a pulse generator 120 and a time delay circuit 122. The current drive waveforms for the microsources 42, 52 are shown in FIGS. 8(a) and 8(c) respectively. FIGS. 8(b) and 8(d) show the detector output waveforms for radiation emanating from the microsources 42 and 52, respectively, if they were to arrive at the detector 44 separately. The combined detector output waveform is shown in FIG. 8(e).

With reference to FIG. 7, the output from detector 44 is amplified by a preamplifier 124 and is then fed into a sample-and-hold circuit 126. The gating pulses to the sample-and-hold circuit 126 are supplied by a pulse generator 128 in synchronism with the pulses generated both by the pulse generator 100 and the time delay circuit 122. These pulses are depicted in FIGS. 8(f) and 8(g), respectively.

Figure 8E:
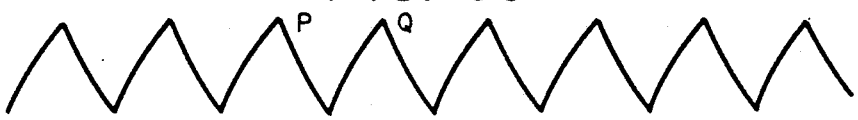
Figure 8F:
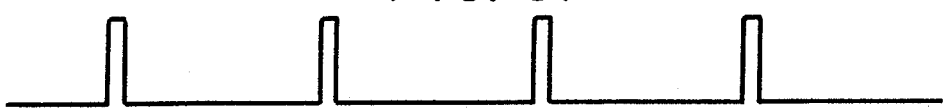
Figure 8G:

As depicted in FIG. 8(e) the signal level $S_P$ sampled at the time P of the respective pulse in FIG. 8(f) should represent the "sample" signal S1 at detector 44 which is sensitive to the presence of $CO_2$ gas in the sample chamber. However, due to the output thermal characteristics of the microsources 42, 52, this signal $S_P$ also contains signal R2 of the reference signal which is a fraction f of the maximum reference signal R3. Therefore, $$\begin{aligned} S_P &= S1 + R2 \\ &= S1 + fR3. \end{aligned}$$

Similarly, the signal level $S_Q$ sampled at or near time Q should represent the "reference" channel signal R3 at detector 44, which is insensitive to the presence of $CO_2$ gas in the sample chamber, but actually also contains signal S2 which is a fraction of the output at S1. Thus, $$\begin{aligned} S_Q &= R3 + S2 \\ &= R3 + gS1. \end{aligned}$$

Figure 9:
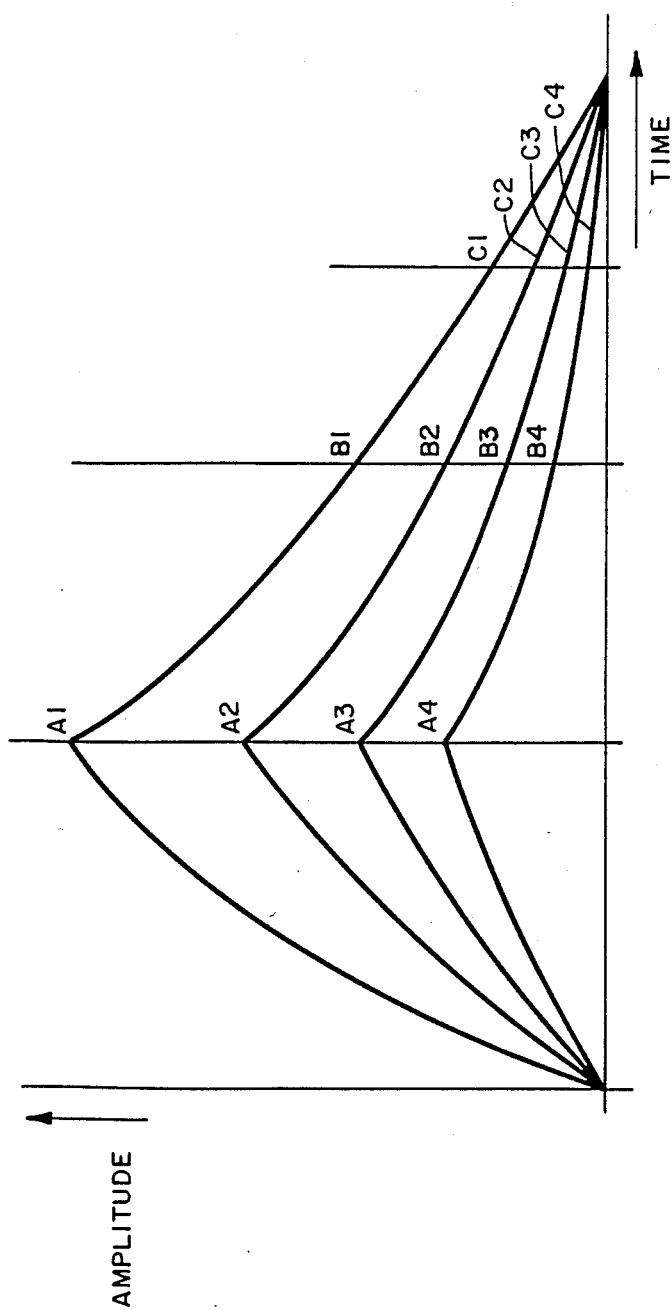
FIG. 9 is a diagram showing the invariance of the microsource output waveshape as seen by the detector in the electronic system of FIG. 7 for four different amplitude levels.

In order to obtain the ratio S1/R3, one needs to know f and g in the expressions for $S_P$ and $S_Q$ above. It has been discovered that one of the salient characteristics of the microsources 42, 52 described above is the amplitude invariance of the output waveform shape as illustrated in FIG. 9. For peak amplitude variation up to a factor of 10, namely $A_1/A_4 = 10$, the ratios $B_1/A_1$ and $C_1/A_1$ are invariant to within 1 part in $10^3$. That is $$B_1/A_1 = B_2/A_2 = B_3/A_3 = B_4/A_4 \text{ and}$$

$$C_1/A_1 = C_2/A_2 = C_3/A_3 = C_4/A_4.$$

Referring back to FIGS. 8(b) and 8(d), the fractions g = S2/S1 and f = R2/R1 ≠ R2/R3 are invariant to a high degree of accuracy (better than $1:10^3$) since the timing relationship is fixed by the sampling pulses depicted in FIGS. 8(f) and 8(g). Thus, if S1 is measured and known, then $S_2 = gS_1$ is determined. Similarly if $R_3$ is measured and known, $R_2 = fR_3$ is also determined. The ratio $S_P/S_Q$ as determined by the sample and hold circuit 126 in FIG. 7 can be digitally interfaced via the standard 1EEE-488 bus 130 to a microprocessor 132 for the calculation of $S_1/R_3$, which is indicative of the $CO_2$ gas concentration in the sample chamber, in accordance with the following formulas:

$$S_1 = S_P - fR_3$$
$$= \frac{S_p - fS_Q}{1 - gf};$$
$$R_3 = S_Q - gS_1$$
$$= \frac{S_Q - gS_P}{1 - gf};$$
$$S_1/R_3 = \frac{S_P - fS_Q}{S_Q - gS_P}.$$

Of course, it should be understood that a wide range of changes and modifications can be made to the preferred embodiments described above. For example, the embodiments can be adapted to measure the concentrations of other gases such as $N_2O$ and methane, for example, by substituting filters of appropriate pass bands. Also, the response time enhancing techniques described above in conjunction with FIG. 4a can be adapted for use with single beam systems. It is therefore intended that the foregoing detailed description be regarded as illustrative rather than limiting, and that it be understood that it is the following claims, including all equivalents, which are intended to define the scope of this invention.

We claim:

1. An optical system for measuring levels of a selected gas, comprising:
    a sample chamber which defines a measuring axis;
    first and second broad band IR sources, each comprising a pair of conductors and a radiating film disposed across the conductors such that current passing between the conductors heats the radiating film;
    a first band-pass filter positioned to filter IR radiation generated by the first IR source to form a measuring beam in which radiation outside of a first IR band aligned with a selected absorption peak of the selected gas is attenuated;
    a second band-pass filter positioned to filter IR radiation generated by the second IR source to form a reference beam in which radiation outside of a second IR band, different from the first IR band, is attenuated;
    a beam splitter positioned to combine the measuring beam and the reference beam and to direct the resulting combined beam through the sample chamber along the measuring axis;
    a detector responsive to the combined beam after it has passed through the sample chamber;
    means for supplying modulated current to the first and second IR sources such that the radiating elements each radiate IR energy in a distinctive time pattern;
    means, responsive to the detector, for generating a first signal indicative of the amplitude of the measuring beam incident on the detector and a second signal indicative of the amplitude of the reference beam incident on the detector; and
    means for combining the first and second signals to determine a measure of the level of the selected gas in the sample chamber.

2. The invention of claim 1 wherein the current supplying means supplies current to no more than one of the IR sources at a time.

3. The invention of claim 1 wherein the current supplying means modulates the current for the first and second IR sources at separate distinctive frequencies.

4. The invention of claim 3 wherein the means for generating the first and second signals comprises first and second frequency selective amplifiers, each adapted to amplify a respective frequency component of the detector signal corresponding to the frequency of a respective one of the measuring and reference beams.

5. The invention of claim 1 wherein the selected gas is $CO_2$, wherein the first IR band is centered at 4.26 microns and wherein the second IR band is centered at 3.6 microns.

6. The invention of claim 5 wherein the sample chamber comprises an airway, and wherein the measure of the level of the selected gas exhibits a time constant less than 0.1 seconds.

7. The invention of claim 1 wherein the separation between the first IR source and the beam splitter is equal to the separation between the second IR source and the beam splitter.

8. The invention of claim 1 wherein the current supplying means modulates current to the first and second IR sources in square waves.

9. The invention of claim 1 wherein the sample chamber comprises an airway.

10. The invention of claim 1 wherein the current supplying means alternately supplies current pulses to the first and second sources, and wherein the means for generating the first and second signals comprises:
    means for sampling the amplitude of the detector signal at sampling times synchronized with the current pulses;
    means for reducing the amplitudes of selected ones of the sampled amplitudes associated with the first IR source by a first factor to generate the first signal; and
    means for reducing the amplitudes of selected ones of the sample amplitudes associated with the second IR source by a second factor to generate the second signal.

11. The invention of claim 1, wherein said detector is the only optical detector in the optical system responsive to IR radiation from the first and second IR sources and supplying information to one or both of the generating means and the combining means.

12. An optical system for measuring levels of a selected gas, comprising:
    a sample chamber which defines a measuring axis;
    a first optical source operative to generate a measuring beam directed along the measuring axis through the sample chamber, said measuring beam comprising radiation at a wavelength corresponding to a selected absorption peak of the selected gas;
    a detector responsive to the measuring beam after it has passed through the sample cell to produce a detector signal;
    means for supplying a time modulated current to the first optical source such that the measuring beam is substantially sinusoidal at frequency $f_1$;

means for combining an $f_1$ frequency component of the detector signal with an additional signal matched in frequency to the $f_1$ frequency component of the detector signal to form a resulting signal having a periodic component at $2 \cdot f_1$ and a low frequency component, wherein the low frequency component varies in amplitude in accordance with the amplitude of the $f_1$ frequency component of the detector signal; and means for measuring the amplitude of the low frequency component of the resulting signal to determine the amplitude of the $f_1$ frequency component of the detector signal.

13. The invention of claim 12 wherein the combining means comprises an analog multiplier which multiplies the $f_1$ component of the detector signal with the additional signal to generate the resulting signal.

14. The invention of claim 12 wherein the $f_1$ frequency component of the detector signal takes the form $A_1(t) \cdot \sin 2\pi f_1 t$, where $A_1(t)$ is a time varying coefficient and t is time;

wherein the additional signal takes the form $A_3 \cdot \sin 2\pi f_1 t$, where $A_3$ is a constant and t is time; and wherein the resulting higher frequency signal takes the following form:

$$A_1(t) \cdot \sin 2\pi f_1 t \cdot A_3 \cdot \sin 2\pi f_1 t = A_1(t) \cdot A_3 (1 - \cos 4\pi f_1 t)/2.$$

15. The invention of claim 12 wherein the combining means comprises a band-pass filter at frequency $f_1$ which isolates the $f_1$ frequency component of the detector signal.

16. The invention of claim 12 further comprising:
a second optical source operative to generate a reference beam having a spectral distribution different from that of the measuring beam;
a beam splitter positioned to combine the measurement beam and the reference beam and to direct the resulting combined beam through the sample chamber along the measurement axis;
means for supplying time modulated current to the second optical source such that the reference beam is substantially sinusoidal at frequency $f_2$, different from $f_1$;
means, responsive to the detector, for determining the amplitude of a $f_2$ frequency component of the detector signal.

17. The invention of claim 16 wherein the selected gas is $CO_2$, wherein the measurement beam is centered at 4.26 microns, and wherein the reference beam is centered at 3.6 microns.

18. The invention of claim 16 wherein the first and second optical sources each comprise a respective broad band IR source comprising a pair of second conductors and a second radiating film disposed across the second conductors such that current passing between the second conductors heats the second radiating film 19. The invention of claim 18 further comprising:
a first band-pass filter positioned to filter radiation generated by the firs IR source of form the measuring beam in which radiation outside a first IR band aligned with a selected absorption peak of the selected gas is attenuated;
a second band-pass filter positioned to filter radiation generated by the second IR source to form the reference beam in which radiation outside a second IR band, different from the first IR band, is attenuated.

20. The invention of claim 12 wherein the additional signal is matched in phase and frequency to the $f_1$ frequency component of the detector signal.

21. The invention of claim 12 wherein the first optical source comprises a first broad band IR source comprising a pair of first conductors and a first radiating film disposed across the first conductors such that current passing between the first conductors heats the first radiating film.

22. The invention of claim 21 further comprising a first band-pass filter positioned to filter radiation generated by the first IR source to form the measuring beam in which radiation outside a first IR band aligned with a selected absorption peak of the selected gas is attenuated.

23. The invention of claim 21, wherein the sample chamber comprises an airway, and wherein the amplitude determining means exhibits a time constant less than 0.1 seconds.

* * * * *

UNITED STATES PATENT AND TRADEMARK OFFICE
CERTIFICATE OF CORRECTION

PATENT NO. : 4,899,053

DATED : February 6, 1990

INVENTOR(S) : N.C. Joseph Lai

Page 1 of 2

It is certified that error appears in the above-identified patent and that said Letters Patent is hereby corrected as shown below:

ON THE TITLE PAGE:

<u>IN THE OTHER PUBLICATIONS</u>

On the cover page, line 4 of OTHER PUBLICATIONS, please delete "Circiuts" and substitute therefor --Circuits--.

In column 1, line 24, after "($CO_2$)" please insert --.--.

In column 1, line 54, after "($pCO_2$)" please insert --.--.

In column 7, line 56, after "sensor" please insert --.--.

In column 7, line 65, after "sensor" please insert --.--.

In column 8, line 26, after "$V_1$" please insert --.--.

UNITED STATES PATENT AND TRADEMARK OFFICE
CERTIFICATE OF CORRECTION

PATENT NO. : 4,899,053

DATED : February 6, 1990

INVENTOR(S) : N.C. Joseph Lai et al.

It is certified that error appears in the above-identified patent and that said Letters Patent is hereby corrected as shown below:

In column 8, line 30, after "waveform" please insert --.--.

In column 9, line 40, after "$4f_2$" please insert --.--.

Signed and Sealed this

Twenty-second Day of September, 1992

Attest:

DOUGLAS B. COMER

Attesting Officer     Acting Commissioner of Patents and Trademarks